United States Patent [19]

Fredberg et al.

[11] Patent Number: 5,666,960
[45] Date of Patent: Sep. 16, 1997

[54] ACOUSTIC IMAGING

[75] Inventors: Jeffrey Fredberg, Sharon; Gary Glass, Boston; John Lehr, Newton, all of Mass.; Bruno Louis, Puteaux, France

[73] Assignees: Hood Laboratories, Pembroke; Biomechanics Inc., Boston, both of Mass.

[21] Appl. No.: 117,176

[22] PCT Filed: Jun. 16, 1993

[86] PCT No.: PCT/US93/05819

§ 371 Date: Mar. 31, 1994

§ 102(e) Date: Mar. 31, 1994

[87] PCT Pub. No.: WO94/09700

PCT Pub. Date: May 11, 1994

Related U.S. Application Data

[63] Continuation-in-part of Ser. No. 808,907, Dec. 17, 1991.

[51] Int. Cl.[6] .................................................. A61B 5/08
[52] U.S. Cl. ............................................................ 128/716
[58] Field of Search ................................ 128/718–721, 128/207.18; 73/574, 589, 597

[56] References Cited

U.S. PATENT DOCUMENTS

| | | | |
|---|---|---|---|
| 3,818,515 | 6/1974 | Neville | 3/1 |
| 4,782,832 | 11/1988 | Trimble et al. | 128/207.18 |
| 4,915,105 | 4/1990 | Lee | 128/207.18 X |
| 4,996,983 | 3/1991 | AmRhein | 128/207.18 X |
| 5,477,852 | 12/1995 | Landis et al. | 128/207.18 |

*Primary Examiner*—Francis Jaworski
*Attorney, Agent, or Firm*—Kane, Dalsimer, Sullivan, Kurucz, Levy, Eisele and Richard

[57] ABSTRACT

Single hand supportable and operable apparatus for providing an output signal characteristic of the morphology of a respiratory tract includes an acoustic pipe for exchanging acoustical energy with the tract. The pipe has an open first end in communication with an opening in the respiratory tract. A transducer, such as a loudspeaker, is coupled to the pipe for launching acoustical energy into the pipe, producing an incident wave towards the opening in the tract and a reflected wave to form a transient wave field in the pipe representative of the morphology of the tract. Preferably, first and second pressure wave sensing transducers, such as microphones, mounted along the length of the pipe in spaced relationship provide first and second transduced signals representative of the transient wave field. A processor processes the first and second transduced signals to provide an output signal characteristic of the morphology of the tract, such as the cross-sectional area as a function of the distance from the opening in the tract.

14 Claims, 4 Drawing Sheets

ACOUSTIC IMAGING

CROSS-REFERENCE TO RELATED APPLICATION

This application is a Continuation-In-Part of copending U.S. patent application Ser. No. 808,907 filed on Dec. 17, 1991.

BACKGROUND OF THE INVENTION

1. Field of the Invention

This invention relates to acoustic imaging of mammalian airway morphology and more particularly concerns noninvasively obtaining a signal representative of the cross-sectional area of an airway (e.g., oral, nasal, or pulmonary) of a subject (e.g., a person or an animal) using electroacoustical transducers.

2. Brief Description of Related Art

A one-dimensional image of the cross-sectional area of an airway as a function of axial position along the airway may be determined from acoustic reflections measured by a single electro-acoustic transducer placed in a position remote from the airway opening. This image is referred to as an area-distance function and is represented by $A(x)$ where $x$ is the axial position along the airway.

Knowledge of the area-distance function, $A(x)$, is useful for example in the diagnosis of mammalian pathologies associated with oral airways, larynx, pulmonary airways, and nasal airways. These pathologies include but are not limited to obstructive sleep apnea, asthma, obstructive pulmonary disease, tracheal stenosis, and nasal septum deviation.

Accurate information about the area-distance function is also useful in the study of airway growth and its disruption and sequelae of bronchopulmonary dysplasia in children.

One approach to using a single electro-acoustic transducer in acoustic imaging is described in U.S. Pat. No. 4,326,416 granted Apr. 27, 1982, to Jeffrey J. Fredberg entitled ACOUSTIC PULSE RESPONSE MEASURING. In all of the single-transducer approaches described previously, a hidden constraint pertains. The associated theories assume implicitly that once propagating to the left within the apparatus, acoustic returns encounter no reflection sites within the wave-tube apparatus itself, which is assumed to be a reflectionless transmission line; there must be no secondary rightward travelling waves and no acoustic reverberation within the wave tube. However, since the loudspeaker is an unavoidable and major reflection site for the wave travelling to the left, the distance separating the loudspeaker from the receiving transducer must be greater than the maximum airway penetration depth of interest; this ensures that secondary reflections from the speaker arrive at the receiving transducer only after data acquisition has been completed. As a result of this distance constraint, imaging instruments for airway imaging previously described in the literature are 1 to 2 meters or more in length (Brooks et al., Reproducibility and Accuracy of Airway Area by Acoustic Reflection, J. Appl. Physiol.: Respirat. Environ. Exercise Physiol. 57(3): 777–787, 1984; D'Urzo et al., Effect of $CO_2$ Concentrations on Acoustic Inferences of Airway Area, J. Appl. Physiol. 60:398–401, 1986); and some are as long as 5 meters (Fredberg J. J. et al., Airway Area From Acoustic Reflections Measured at the Mouth, J. Appl. Physiol.: Respirat. Environ. Exercise. Physiol. 48(5): 749–758, 1980).

A two-transducer approach is described in a paper of M. R. Schroeder entitled "Determination of the Geometry of the Human Vocal Tract by Acoustic Measurements" in J. Acoust. Soc Am. 41(4), 1002–10 (1967). However, as with the single-microphone approach, Schroeder's two-microphone method was never embodied successfully into a small, compact, hand holdable light-weight working apparatus and in fact never achieved airway reconstructions from human or animal airways.

The present invention is based upon a new two-transducer method and a new associated theory that permits practical application of airway reconstructions by acoustic reflections. Because this theory explicitly incorporates reverberation within the wave tube and does not demand non-overlapping time windows of incident and reflected waves, it removes the distance constraint described above, permitting placement of the loudspeaker or launching transducer close to the receiving transducers.

As such, the new theory allows fabrication of a practical miniature apparatus whose overall length is only a few centimeters rather than meters. The apparatus can image the respiratory tract of mammalian subjects, including the nasal oral and pulmonary cavities.

SUMMARY OF THE INVENTION

In an assembly for acoustically imaging the internal morphology of portions of the respiratory tract of a mammal, including a human, the improvement which comprises a light-weight, easy to manipulate, hand-held acoustic imaging head which is rugged and entirely hand supportable and operable by an operator, throughout an imaging procedure, which head comprises;

A. a rugged hand-holdable housing having
   1. an elongate body, defined by
      (a) a top end;
      (b) a base end;
      (c) an outer wall extending between the top end and the base end; and
      (d) an internal chamber;
   2. an aperture through the housing top end, providing fluid communication between the internal chamber and the outside of the housing; and
   3. a shape and configuration of the outer wall facilitating gripping of the housing with a human hand;
B. an acoustic pipe for transmitting acoustical energy and receiving the reflected acoustical energy, mounted in the aperture, said pipe having a first end within the chamber and an open second end outside of the housing, said second end of the acoustic pipe being adapted for connection of the acoustic pipe to an orifice leading into the respiratory tract;
C. a launching transducer mounted in the chamber and coupled to the first end of the acoustic tube, for launching acoustical energy into the acoustic pipe, propagating an incident wave out of the open second end;
D. at least one acoustic pressure wave sensing transducer mounted on the acoustic pipe at a location between the first and second ends of the acoustic pipe, for sensing reflections of the incident wave, received back in the acoustic tube through the open second end and generating a signal; and
E. means at least partially within the chamber, connected to the acoustic wave sensing transducer, for transmission of signals transduced, to processor means for processing said signals into a processor output signal characteristic of the morphology of a site within the mammal's respiratory tract.

The invention provides signals representative of airway morphology in apparatus that is relatively small and portable. The invention may be used for diagnostic and screening purposes in a confined area such as a laboratory, a doctor's office, a place of work, and at bedside.

BRIEF DESCRIPTION OF THE DRAWINGS

FIG. 3 is a fragmentary view of the outside wall of the housing for the embodiment head of the invention of FIG. 1, showing a representative control panel.

DETAILED DESCRIPTION OF THE PREFERRED EMBODIMENTS OF THE INVENTION

Those skilled in the art will gain an appreciation of the invention from a reading of the following description of the preferred embodiments when viewed with the accompanying drawings of FIGS. 1–7, inclusive.

Figure 1:
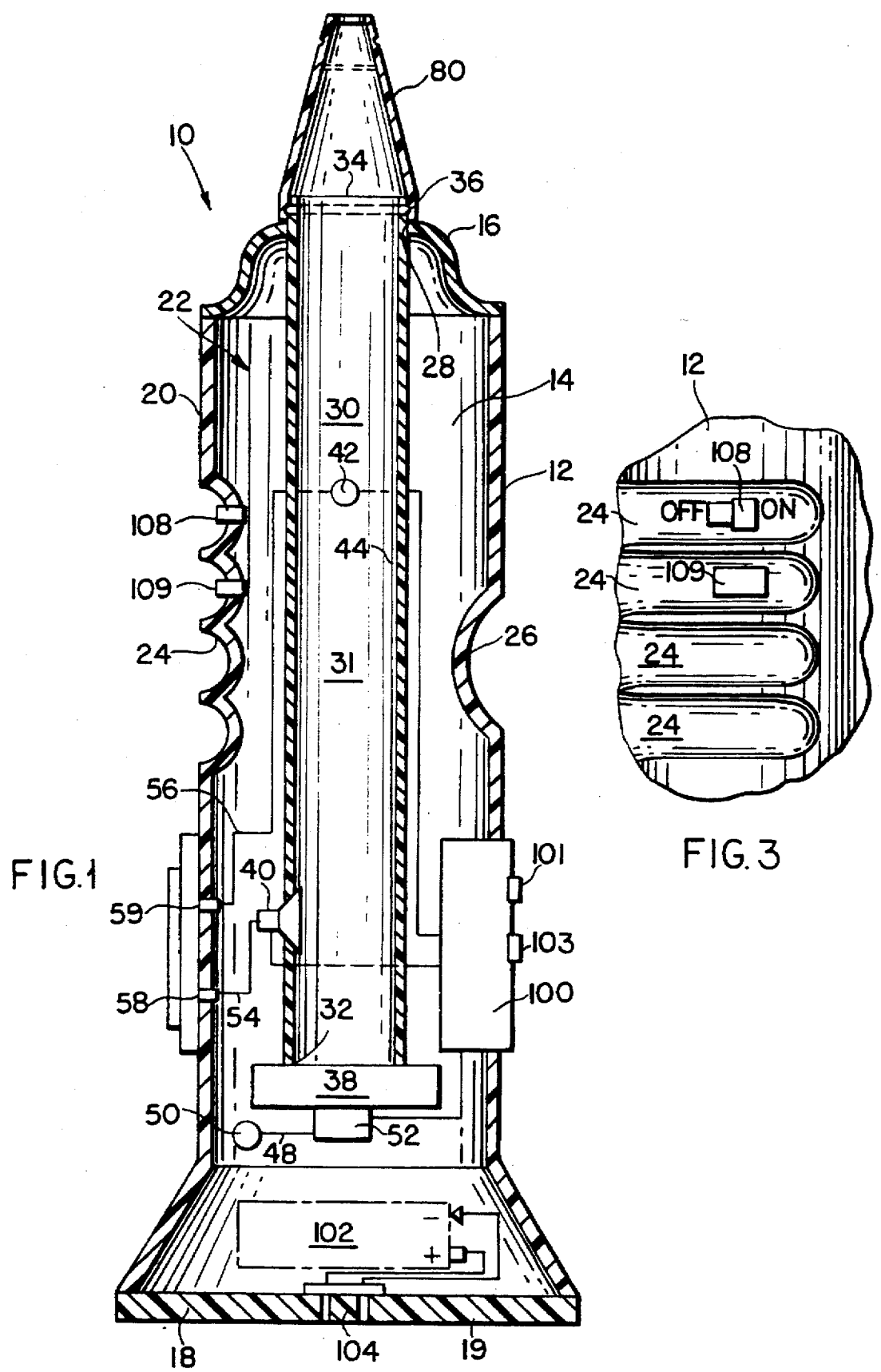
FIG. 1 is a cross-sectional side elevation of a preferred embodiment head of the invention.

Referring first to FIG. 1, a cross-sectional side elevation, there is seen a preferred embodiment acoustic imaging head 10 of the invention for imaging the internal morphology of portions of the respiratory tract of a mammal, including a human. Head 10 comprises a hand-holdable housing 12 having an elongate body 14 defined by a top end 16 and a base end 18 which presents a planar surface 19 for standing the head 10 on a flat surface in an upright position. The housing 12 presents an outer wall 20 extending between ends 16, 18 and defining an internal, closed chamber 22. Wall 20 advantageously includes integrally molded finger holds 24 and a palm grasping indentation 26. The outside surface of wall 20 may be a frictional surface to facilitate holding and operating the head 10 by a single human hand. The overall weight of head 10 will be such that it is light and easy to operate and manipulate. The head 10 is fully supportable by hand-holding by the operator. An aperture 28 pierces end 16 of the housing 12. The aperture 28 has mounted therein end 34 of an acoustic pipe 30 having a closed first end 32 within chamber 22 and an open end 34 outside of the housing 12. The end 34 of acoustic pipe 30 includes a rib 36 encircling the circumference of end 34, which functions as a means for coupling to the acoustic pipe 30 an adaptor in the form of coupling device 80 for mating with an orifice of the mammal respiratory tract for imaging. The acoustic pipe 30 substantially traverses chamber 22 and its dimensions dictate the overall dimensions of the housing 12. For example, the acoustic pipe 30 is advantageously about 2.0 to 4.0 cm, preferably about 1.2 cm in diameter and has a length of between about 5 to about 40 cm, most preferably 5 to 20 cm. The end 32 of pipe 30 is closed by mounting thereon a loudspeaker or launching transducer 38 which, upon energization, will launch acoustic energy into the interior of acoustic pipe 30, propagating an incident sonic wave towards open end 34 of pipe 30 and outside the end 34. When the head 10 is coupled to an orifice in the respiratory tract for imaging through coupling device 80, the propagated sound wave will enter the respiratory tract, strike anatomical features in the tract and be reflected back through end 34 into the interior of acoustic pipe 30 to form a transient wave field within the pipe 30. This wave field is representative of the morphology of the respiratory tract. Two spaced apart pressure transducers 40, 42 (such as Endevco series 8510 B microphones) are mounted on the acoustic pipe 30 with their pressure sensor flush with the inner walls of acoustic pipe 30 in order to reduce parasitic acoustic reflections. The transducers 40, 42 are advantageously separated from each other a distance of from about 1.0 to about 15 cm. and both are separated from the end 34 of acoustic pipe 30 by at least about 2.0 cm. When the head 10 is to be used only for the imaging of relatively shallow cavities, i.e.; interior respiratory tract cavities which are to be imaged and which are close to the transducer (at most about 2 to 3 cm.), such as the nasal vestibule, only one of the transducers 40, 42 need be present or active. However, when only one of the transducers 40, 42 is employed to sense reflected acoustical waves it is necessary to calibrate the head 10 for each imaging as will be described more fully below. The launching transducer 38 is energized to transmit a one-dimensional, essentially lossless acoustic wave into the acoustic pipe 30 by an electrical signal transmitted via conductor 48 which may terminate externally in a plug-type connector 50 mounted on the housing 12 wall 14 and in an amplifier 52 which will be described more fully hereafter. The transducers 40, 42 are each electrically connected by separate electrical conductors 54, 56, respectively, which also can terminate in plug-type connectors 58, 59 mounted on the housing 12 wall 14. The connectors 58, 59 can be used for connection to signal processing means external of head 10, as will be discussed more fully hereinafter.

Figure 2:
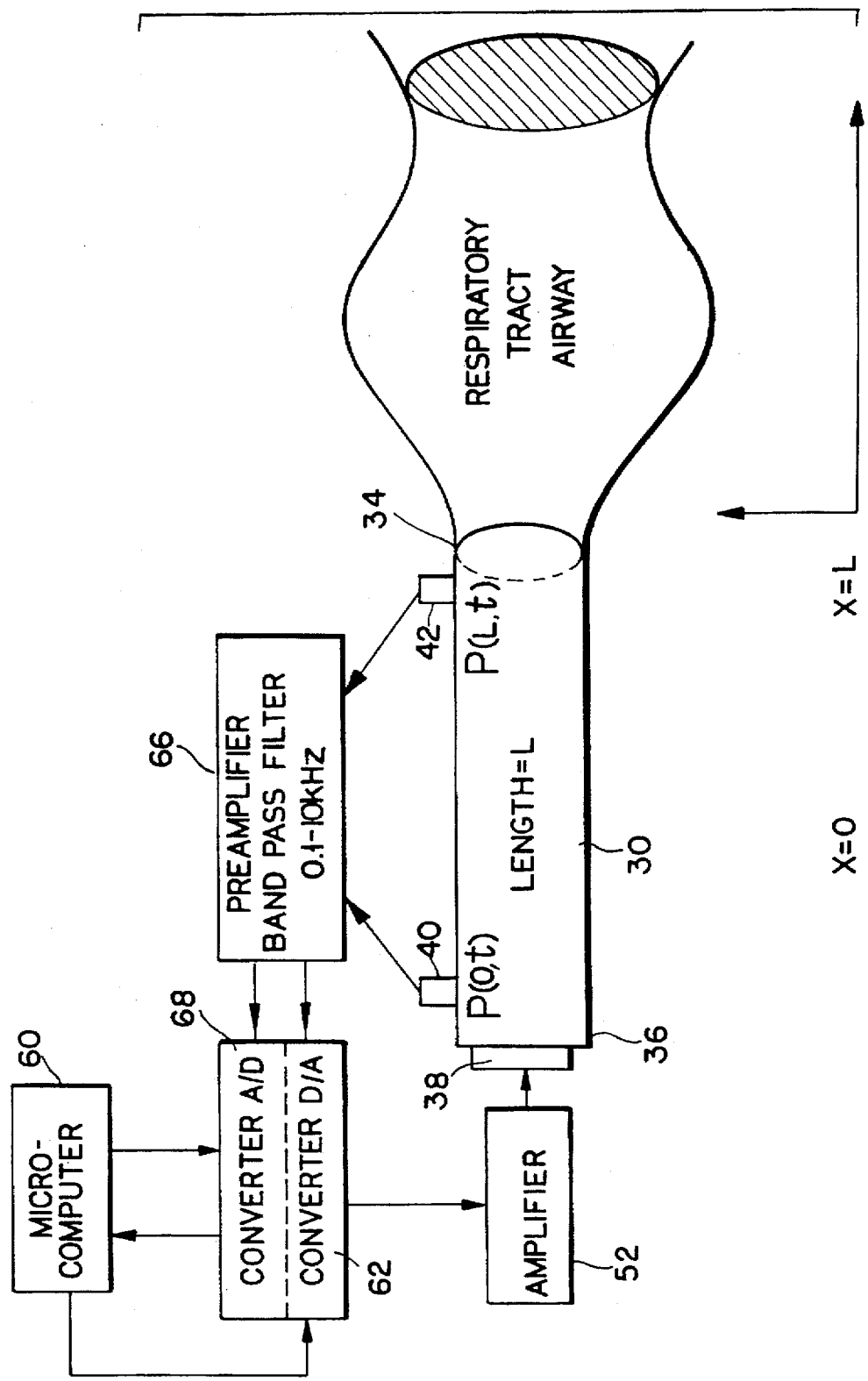
FIG. 2 is a combined block-pictorial diagram illustrating operation of the head shown in FIG. 1.

In one embodiment head 10 of the invention, the connectors 50, 58, 59 are connectable through a communications cable to a signal processor, including a host computer (not shown in FIG. 1) which is remote from the head 10. In this embodiment, the mode of the operation will be described with reference to FIG. 2 as follows. FIG. 2 is a combined block-pictorial diagram illustrating the operation of an imaging system using the head 10 of the invention.

Referring to FIG. 2, a simplified assembly includes as the launching transducer 38 a loudspeaker such as model MDR 434. Acoustic pipe 30 is of length L. First receiving transducer 40 is located at x=o where x is the axial position along pipe 30, second receiving transducer 42 is located at x=L, adjacent the airway (e.g. an oral, nasal, or pulmonary airway) of a subject mammal. Transducer 38 launches a one-dimensional essentially lossless acoustic wave into pipe 30, towards x=L. The launched incident wave travels through pipe 30 and into the airway. A reflected wave, or echo, representative of gradients in the acoustic impedance in the airway then propagates back into pipe 30 towards launching transducer 38. Receiving transducers 40 and 42 individually and together sense the pressure waves associated with the echo and provide transduced electrical signals representative of the incident and reflected waves for processing by microcomputer 60.

Microcomputer 60 generates a digital probe signal converted to an analog signal by D/A converter 62, and amplified by amplifier 52 to drive launching transducer 38 and launch the incident probe acoustic wave. The transduced outputs from receiving transducers 40 and 42 are band-pass filtered by preamplifier 66 and then converted by A/D convertor 68 into digital signals. Microcomputer 60 stores these digital signals in its RAM capability.

Microcomputer 60 processes the stored digital signals to provide an output signal A(x), i.e., a one-dimensional image of the cross-sectional area of the airway as a function of axial position, x, along the airway. Computer 60 preferably processes these signals in accordance with the Ware-Aki algorithm ("Continuous and Discrete Inverse Scattering Problems in a Stratified Elastic Medium. I. Plane Waves at Normal Incidence", J. Acoust. Soc. Am., 54, 4, 911–921, 1969) to provide the area distance function, A(x), from the impulse response of the airway, h(t). The relationship between the pressure field and h(t) may be derived as follows. The pressure field within the tube in the domain $0 \leq x \geq L$ can be described as the superposition of two one-dimensional waves propagating with the same wave speed but in opposite directions as given by $$p(x,t) = p_r(x,t) + p_l(x,t) \tag{1}$$

where t is time, $p_r$ is the incident wave propagating to the right (i.e., from x=o towards x=L), and $p_l$ is the reflected wave propagating to the left (i.e., from x=L towards x=o).

The pressure conditions at x=o and x=L are given by $$p_l(L,t) = p_r(L,t) * h(t) \tag{2}$$

and $$p_r(o,t) = p_l(o,t) * s(t) \tag{3}$$

where s(t) is the impulse response of the loudspeaker and * denotes the convolution operation. Given that a one-way propagation delay is $\tau = L/v$ where v is the velocity of sound, the following relationships exist:

$$p_l(o,t) = p_l(L, t-r) \tag{4}$$

$$p_r(L,t) = p_r(o, t-r). \tag{5}$$

Equations (1) through (5) may be combined by mathematical techniques well-known in the art (e.g., the Fourier transform, and algebra) to yield $$h(t) * \{p(o,t) - p(L, t-\tau)\} = p(L, t+\tau) - p(o,t) \tag{6}$$

and $$h(t) * s(t) = \delta(t - 2r). \tag{7}$$

Equation (7) indicates that both waves propagate with an equal, non-zero delay. In equation (7), the symbol $\delta$ denotes the well-known impulse function which is sometimes called the delta function. Equation (6) identifies the relationship between the pressure field and h(t). Equation (6) may be discretized by the Riemann sum approximation to yield $$h(n\Delta t) = \{1/p(o,o)\}\{p(L, (m+n)\Delta t) - p(o, n\Delta t)\} - \tag{8}$$

$$\left\{ \sum_{k=1}^{k=n} h((n-k)\Delta t)/p(o,o) \right\} \{p(o, k\Delta t) - p(L, (k-m)\Delta t)\}$$

where $\Delta t$ is the sampling duration of the time discretization, n is the set of integers 1, 2, 3, etc., m is an integer such that $\tau = m\Delta t$, p(o,o) denotes the first non-zero pressure value at x=o, k is the index of the summation, and the lower and upper limits of summation are, respectively, k=1 and k=n.

In brief summary, microcomputer 60 processes the stored digital data signals representative of the transduced signals from the spaced-transducers 40,42 to provide a signal representative of the impulse response of the airway, h(t), according to equation (8). Microcomputer 60 then processes the signal h(t) in accordance with the Ware-Aki algorithm to provide a signal, A(x), representative of the morphology of the airway. The signal A(X) can then be stored in the storage capability of microcomputer 60 for future call-up when comparisons are desired, to subsequent images.

The wave propagation in pipe 30 may be assumed lossless. The early portions of the transduced pressures at x=o and x=L are then identical except for the propagation delay t. Microcomputer 60 may determine the propagation delay by minimizing mean square differences between the transduced signals in the early part of their respective transients. The relative gain of the transducers may be determined in a similar manner. To obtain sufficient time resolution, microcomputer 60 preferably interpolates the transduced signals to achieve an effective sampling period of 0.75 μs (i.e., $\Delta t = 0.75$ μs).

Equation (8) requires preferably the propagation delay to be an integral multiple of the sampling period t, i.e. $\tau = m\Delta t$. Microcomputer 60 preferably interpolates and resamples digitized transduced signals such that the propagation delay corresponds to 24 time steps, i.e., $\tau = 24\Delta t$. This value of the propagation delay corresponds to a spatial step increment of about 0.2 cm.

In providing h($\Delta t$) in accordance with the equation (8), the first non-zero pressure value p(o,o) is preferably larger than some minimal threshold value to maintain stability. The pressure values occurring before this first threshold pressure are initially neglected to obtain a first approximation of h(t). To de-emphasize errors that may be introduced by the threshold it is advantageous to provide a corrected h($\Delta t$) characterized by increased stability and accuracy by convolving the first approximation of h(t) with the digitized pressure values occurring prior to the first non-zero pressure (i.e., the pressure values that were initially neglected). Microcomputer 60 then preferably bandpasses the discrete values sequence h(n$\Delta t$) that represents the impulse response of the airway h(t) with a digital, linear-phase, finite impulse response (FIR) filter having a passband from 0.01 kHz to 9 kHz to attenuate physiologic noise associated with airway wall non-rigidity, instability of the impulse response, h($\Delta t$), and artifacts associated with acoustic cross-modes.

Microcomputer 60 then processes the corrected h($\Delta t$) signal in accordance with the Ware-Aki algorithm to provide an output signal representative of the area-distance function, A(x), of the airway graphically represented.

The microcomputer 60 (such as Compuadd model 320 with an Intel 80386 microprocessor operating at 20 MHz) is coupled to a converter module having a 12-bit analog-to-digital (A/D) converter 68 with a sampling period typically of 24.0 μs and a 12 bit digital-to-analog (D/A) converter 62 coupled to pre-amplifier 66 typically with a band-pass filter having a passband from 0.1 kHz to 10.0 kHz (such as Tektronix model AM 502) that is coupled to transducers 40 and 42. D/A converter 62 is coupled to transducer 38 through amplifier 52.

As mentioned above, when the head 10 of the invention is to be used for imaging relatively shallow body cavities near the orifice for coupling to the head 10, for example, the nasal vestibule to a depth of about 1 to 3 cm., one can use a head 10 where only one of the transducers 40, 42 is present or active. In this case, the relationship between the pressure field and h(t) may be derived as described in the U.S. Pat. No. 4,326,416 which is incorporated herein by reference thereto. As also mentioned above, with only one operative receiving or sensing transducer, it is necessary to calibrate the instrument. This calibration procedure is also described fully in the U.S. Pat. No. 4,326,416. An advantage of the preferred two transducer (microphone) apparatus of the invention is the dispensation with of the calibration procedure requirement.

The microcomputer 60 may also be coupled electronically to the input terminals of a display module (not shown in FIG. 1 or 2) for visual display of processed signals from the transducers 40, 42. Alternatively or in addition, the processed signals can be input to a conventional printer for a printed record of the imaging results. Simultaneous visual display of processed signals is advantageous to the operator and permits the operator to practice a preferred method of operation. It will be appreciated by those skilled in the art that a hand operated device for use in imaging, for example, the nasal passages of a mammal requires a steady operator's hand and patient-subject to obtain consistently good and reproducible signal data. Slight inopportune movement on the part of the operator or patient can generate faulty data. The operator with experience can see on a visual display, inconsistent signals and periods of time when a series of incident waves propagated by the head are reflected, sensed and processed as consistent signals representative of the desired image. The operator in fact may have to manipulate the head 10 into certain positions in order to obtain consistent and reproducible signals (for example when a good coupling seal is difficult to achieve between the orifice and head 10). To overcome this problem, the head 10 is advantageously used in a "pre-trigger" mode to sort out good signals from faulty signals, i.e.; inconsistent signals. This is done by use of a "circular buffer" whereby the microprocessor 60 is programmed to only store in the RAM the last 10 of 10 plus X signals received from A/D converter 68 (first in, first out). These last 10 signals can represent a collection time period of about 2 seconds. When the operator views the signals processed and put out by the microprocessor 60, as consistent, the operator can stop acquisition of new signals to maintain the last 10 consistent signals in the microprocessor memory for storage and future call-up. In this way, the useful signals are stored for later recall.

In a most preferred embodiment head 10 of the invention, electrical power and/or communication cables between the head 10 and the signal processing components of the imaging system described above are eliminated. The imaging system will then be self-contained in the single hand-held device of the invention. Referring again to FIG. 1, miniature signal processing means 100 is mounted in the chamber 22 and includes the pre-amplifier 66, converter D/A 62 and converter A/D 68 with microcomputer 60. Integration of the computer circuitry into from one to three chips enables this miniaturization. A rechargeable battery 102 such as an AAA size battery is advantageously mounted in chamber 22 proximal to the housing base end 18 and includes a socket 104 for electrical recharge by connection to AC wall outlet sources. The battery pack 102 is electrically connected to the processing means 100 and the launching transducer 38, as a power source, controlled by switch circuitry described below (wiring not shown in FIG. 1; see FIG. 4). The connectors 101, 103 are for connection of means 100 to a visual display monitor for observation and/or to a printer for obtaining a printed record of the processed signals.

Referring to FIG. 3, a portion of the outside of housing 12 wall 14 is shown, with a control 108 for energization and operation of the head 10, located in one of the fingerholds 24 to facilitate one-handed operation of head 10. For the sake of brevity, a switch 109 is located in an adjacent fingerhold 24, which may be used to control such functions as START ACQUISITION OF DATA; STOP ACQUISITION OF DATA; DISPLAY DATA; SELECT DATA FOR DISPLAY; STORE DATA; RECALL DATA FOR DISPLAY; COMPARE NEW DATA TO RECALLED DATA, etc. Any and all of these functions (and others) can be controlled by finger-operated switches. The electrical wiring necessary for these control functions are not shown in FIG. 1, for clarity of the drawing, but will be conventional and realized by those skilled in the art of electrical wiring.

Figure 4:
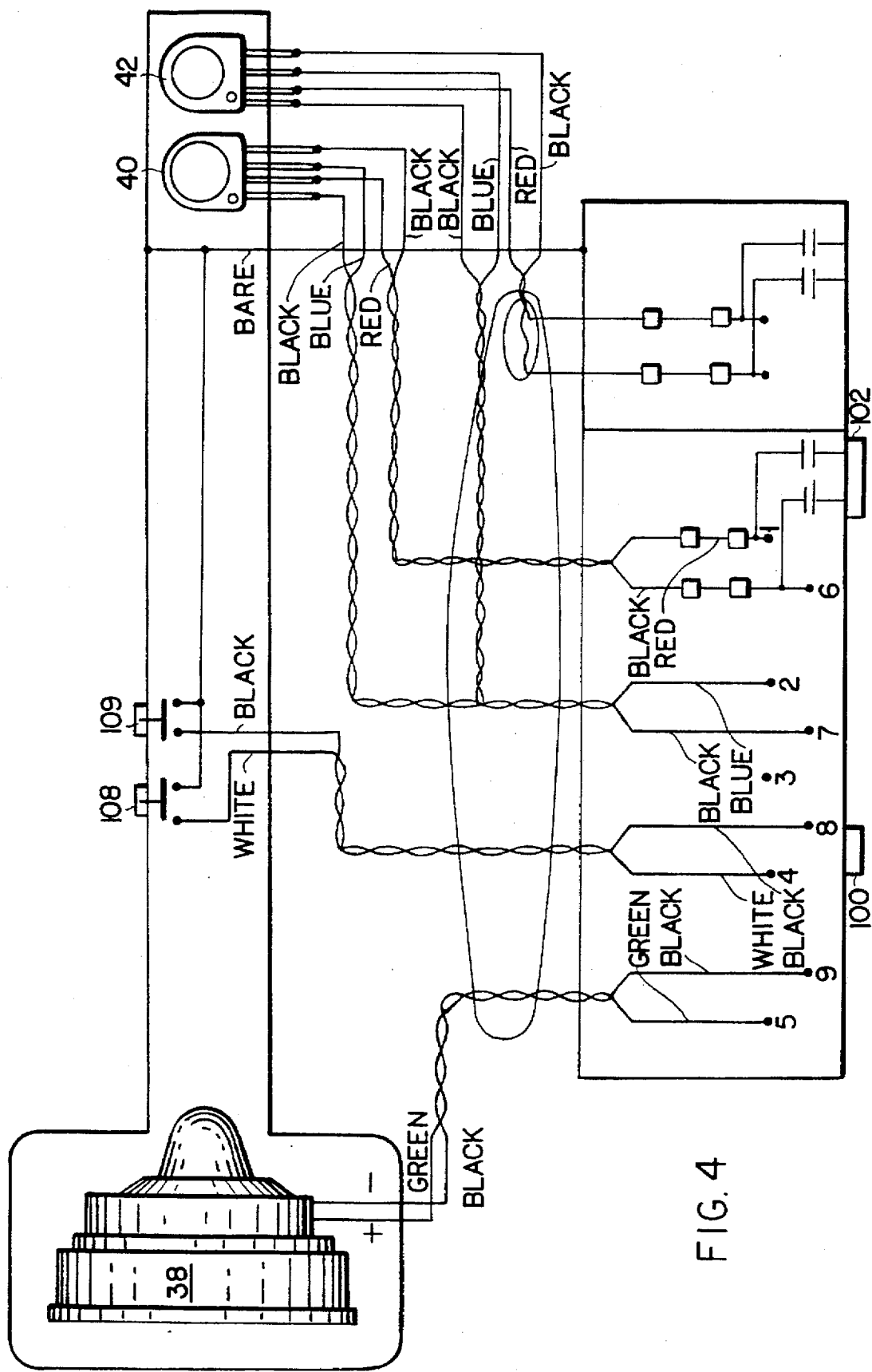
FIG. 4 is an electrical wiring diagram for the embodiment head shown in FIG. 1.

FIG. 4 is a wiring diagram for the preferred embodiment head 10 described above, which is completely self-contained.

Figure 5:
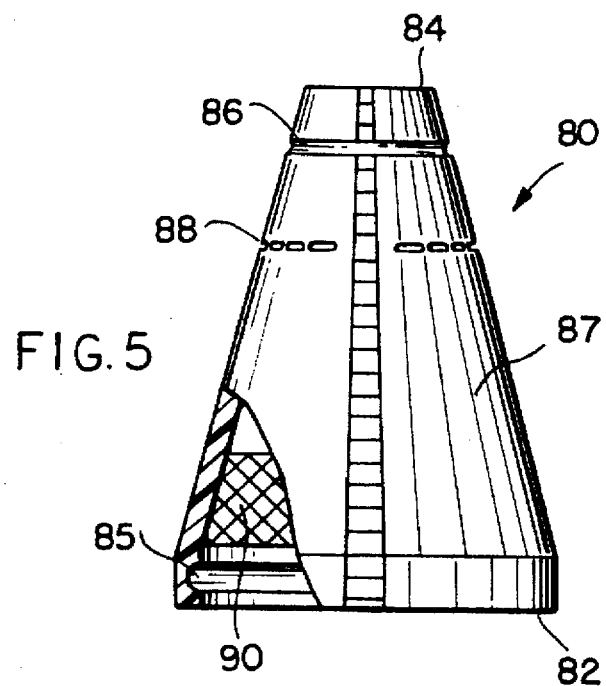
FIG. 5 is a partially fragmented sideview of a disposable nasal coupling device of the invention used in conjunction with the head of FIG. 1.

Referring to FIG. 5 there is shown in a partially fragmented side view, a sterilizible, disposable nasal coupling device 80 having an input end 82 that attaches to the output end of pipe 30 and an output end 84 for insertion into a nostril. Channel 85 on the inside wall of coupling device 80 mates with and receives the rib 36 on end 34 of tube 30, for secure, removable attachment. Channel 85 and rib 36 cooperate to provide a means for attaching the acoustic pipe 30 end 34 to the coupling device 80. Other means of attachment will be apparent to those skilled in the art, such as the so-called "bayonet mount", screws, frictional fits, male-female connectors and the like. Nasal coupling device 80 may have output ends 84 of different sizes for snug sealing engagement with the inside of nostrils of different sizes. Its internal area contour is such that impedance matching between subject and apparatus is maintained with maximum acoustic energy transmission.

Figure 6:
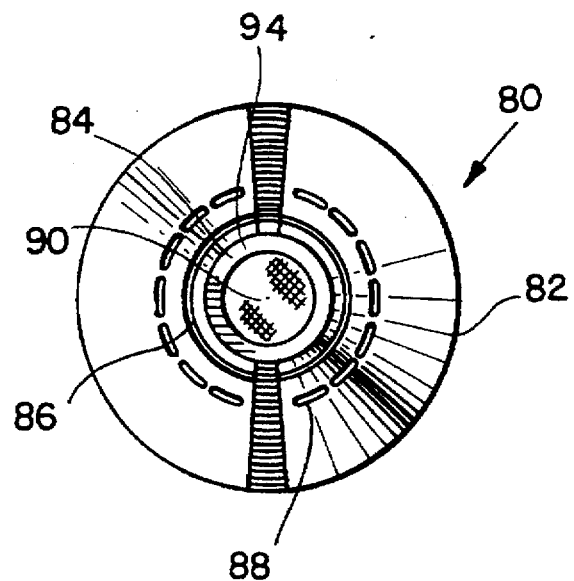
FIG. 6 is a view from above of the coupling device shown in FIG. 5.

FIG. 6 is a top view of the coupling device 80 shown in FIG. 5 and shows that the rim or edge 94 of end 84 may be relatively thin, i.e.; on the order of about 0.5 to about 1.5 mm in uniform thickness for a distance of about 10 mm from the edge 94 toward end 82 to facilitate a comfortable fit within the nostril and to allow trimming circa 10 mm off the length of the device 80. The wall 87 thickness below the 10 mm distance from the edge 94 may be increased towards end 82, where more structural stability and less flexibility is desired. The wall 87 of the oval shaped device 80 (as seen from above in FIG. 6) tapers from end 82 inwardly to end 84, on an inward slope of about 10° to 15° from the perpendicular. Similarly, there may be disposable coupling devices with output ends 84 of different sizes for snugly coupling to other airway orifices of different sizes, including the mouth.

The preferred coupling device 80 may be fabricated from a wide variety of materials, both flexible, and inflexible in character. Representative of such materials are a wide range of synthetic and natural polymeric resins, preferably having properties which do not inhibit passage of acoustic waves through the device 80 from and to the pipe 30. Thus, the device 80 is advantageously fabricated from polycarbonate resins, polyvinyl chloride, polyvinyl alcohol, ABS resins, polystyrene, polyurethane, polytetrafluoroethylene, natural rubber and like resins. A preferred material is a flexible polysilicone rubber, for sealing engagement with an orifice to be used. Indicia such as line 86 can be placed on the device 80 to indicate the depth of desired insertion into the nostril which is preferably 2 to 3 mm penetration at most. This is advantageous to insure accurate imaging. Also, scribe marks 88 can be placed on the device 80, indicating where the device 80 can be cut to trim it for a larger sized nostril. A vertical rib or mark on the axial line of device 80 may be placed on the outside body of device 80 as a reference mark or indicia to facilitate placing the device 80 in position on a patient's nose, removing it and replacing it in the same position for subsequent imaging. Note that the device 80 can also be fitted internally with a filter 90 which does not inhibit passage of sound waves, but will stop passage of fluids such as mucous.

Figure 7:
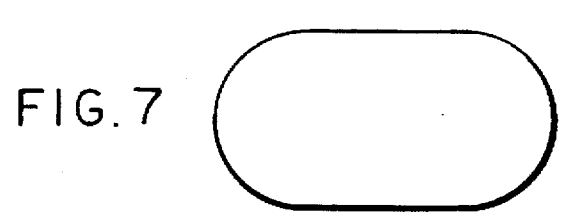
FIG. 7 is an alternative shape for the coupling opening in the device of FIG. 5.

The opening of device 80 at end 84 as shown in FIG. 6 is round (oval) as defined by the wall 87. The shape of the opening may be circular, of any shape including perfectly round, oblong or shaped like a race-track having a greater dimension in one direction. FIG. 7 shows a preferred circular shape for the opening of a device 80 at end 84. The geometry of the end 84 of device 80 preferably matches the geometry of the orifice to be coupled without any substantial distortion of the nasal vestibule.

The invention is not to be limited to the description of the preferred embodiment described above, but include within the spirit and scope of the invention other embodiments.

For example, pipe 30 (FIG. 1) could be 1.2 cm in diameter and 10 cm in length. In this case, the two transducers are preferably separated by 3.0 cm but transducer 18 is still located 2.0 cm from the airway opening. With the 10 cm length tube, the propagation delay, $\tau$, is made to correspond to seven time steps, i.e.; $\tau = 7\Delta t$. This value of the propogation delay corresponds to a spatial step increment of about 0.2 cm.

Also, an algorithm other than the Ware-Aki algorithm could be used to uniquely determine the area-distance function A(x), of the airway from h(t). Also, algorithms other than the equation (8) above can be used to determine h(t) from the pressure field.

What is claimed:

1. In an assembly for acoustically imaging portions of the internal morphology of the respiratory tract of a mammal, including a human, the improvement which comprises a lightweight, easy to manipulate, hand-held acoustic imaging head which is rugged and entirely hand supportable and operable by an operator, throughout an imaging procedure, which head comprises;
    A. a rugged hand-holdable housing having
        1. an elongate body, defined by
            (a) a top end;
            (b) a base end;
            (c) an outer wall extending between the top end and the base end; and
            (d) an internal chamber;
        2. an aperture through the housing top end, providing fluid communication between the internal chamber and the outside of the housing; and
        3. a shape and configuration of the outer wall facilitating gripping of the housing with a human hand;
    B. an acoustic pipe for transmitting acoustical energy and receiving the reflected acoustical energy, mounted in the aperture said pipe having a first end within the chamber and an open second end outside of the housing, said second end of the acoustic pipe being adapted for connection of the acoustic pipe to an orifice leading into the respiratory tract;
    C. a launching transducer mounted in the chamber and coupled to the first end of the acoustic tube, for launching acoustical energy into the acoustic pipe, propagating an incident wave out of the open second end;
    D. at least one acoustic pressure wave sensing transducer mounted on the acoustic pipe at a location between the first and second ends of the acoustic pipe for sensing reflections of the incident wave, received back in the acoustic tube through the open second end and generating a signal; and
    E. means at least partially within the chamber, connected to the acoustic wave sensing transducer, for transmission of echo signals transduced, to processor means for processing said echo signals into an acoustic image signal characteristic of the morphology of a site within the mammal's respiratory tract.

2. The head of claim 1 which further comprises a coupling device mounted on the open second end of the acoustic pipe, for coupling the head to an orifice in the respiratory tract.

3. The head of claim 2 wherein the device is adapted by size and configuration to couple with the nostril of a mammal.

4. The head of claim 1 wherein the acoustic pipe has a length of from about 5 to about 15 cm.

5. The head of claim 1 wherein the first and second pressure-wave sensing transducers are spaced apart from each other by a distance of from about 1 to about 15 cm.

6. A light weight, easy to manipulate with one hand, hand-holdable and operable acoustic imaging device for acoustically imaging portions of the internal morphology of the respiratory tract of a mammal, which comprises;
    A. a rugged hand-holdable housing having
        1. an elongate body, defined by
            (a) a top end;
            (b) a base end;
            (c) an outer wall extending between the top end and the base end; and
            (d) an internal chamber;
        2. an aperture through the housing top end, providing fluid communication between the internal chamber and the outside of the housing; and
        3. a shape and configuration of the outer wall facilitating gripping of the housing with a human hand;
    B. an acoustic pipe for transmitting acoustical energy and receiving the reflected acoustical energy, mounted in the aperture, said pipe having a first end within the chamber and an open second end outside of the housing, said second end of the acoustic pipe being adapted for connection of the acoustic pipe to an orifice leading into the respiratory tract;
    C. a launching transducer mounted on the housing and coupled to the first end of the acoustic tube, for launching acoustical energy into the acoustic pipe, propagating an incident wave out of the open second end;
    D. at least first and second acoustic pressure wave sensing transducers mounted on the acoustic pipe at locations between the first and second ends of the acoustic pipe in spaced relationship from each other, for sensing reflections of the incident wave, received back in the acoustic tube through the open second end and generating a signal;
    E. means connected to the acoustic wave sensing transducers, for transmission of signals transduced, to processor means for processing said signals into a processor output signal characteristic of the morphology of a site within the animal's respiratory tract;
    F. means connected to the launching transducer for energizing the launching transducer;
    G. means for processing the generated signal from the transducers into an output signal characteristic of the morphology of a site within the animal's respiratory tract.

7. The device of claim 6 wherein the processor means is mounted on the housing.

8. The device of claim 6 which further comprises a power source mounted in the housing for energizing the launching transducer.

9. The device of claim 6 wherein the acoustic pipe has a length of from about 5 to about 40 cm.

10. The device of claim 9 wherein the first and second pressure-wave sensing transducers are spaced apart a distance of from about 1 to about 15 cm.

11. The device of claim 6 which further comprises a coupling device for sealing engagement of the open end of the acoustic pipe with an orifice into the respiratory tract.

12. The device of claim 11 wherein the coupling device is fabricated from a polysiloxane rubber.

13. The device of claim 1 which further comprises a display means for displaying graphically an image generated by the output signal.

14. The device of claim 1 wherein controls for the processing means are positioned on the housing at sites accessible to the operator's hand hold.

* * * * *